United States Patent [19]
Crook

[11] Patent Number: 5,304,210
[45] Date of Patent: Apr. 19, 1994

[54] APPARATUS FOR DISTRIBUTED BONE GROWTH STIMULATION

[75] Inventor: David F. Crook, Garland, Tex.
[73] Assignee: AMEI Technologies Inc., Wilmington, Del.
[21] Appl. No.: 827,002
[22] Filed: Jan. 28, 1992
[51] Int. Cl.[5] ............................................. A61N 1/18
[52] U.S. Cl. ................................................. 607/51
[58] Field of Search ......................... 128/419 F, 419 R

[56] References Cited

U.S. PATENT DOCUMENTS

| | | | |
|---|---|---|---|
| 3,745,995 | 7/1973 | Kraus | 128/419 F |
| 3,842,841 | 10/1974 | Brighton et al. | 128/419 R |
| 4,027,392 | 6/1977 | Sawyer et al. | 32/10 A |
| 4,403,606 | 9/1983 | Woo et al. | 128/92 |
| 5,000,166 | 3/1991 | Karpf | 128/69 |
| 5,030,236 | 7/1991 | Dean | 623/16 |
| 5,123,898 | 6/1992 | Liboff et al. | 600/13 |

FOREIGN PATENT DOCUMENTS

| | | | |
|---|---|---|---|
| 0383992 | 8/1990 | European Pat. Off. | A61K 47/48 |
| 313248 | 2/1983 | Fed. Rep. of Germany | A61N 1/36 |
| 2178143 | 11/1973 | France | A61F 5/04 |
| 2199967 | 4/1974 | France | A61F 1/24 |

Primary Examiner—William E. Kamm
Assistant Examiner—Scott M. Getzow
Attorney, Agent, or Firm—Baker & Botts

[57] ABSTRACT

Apparatus for promoting healing in a bony structure having an injury is provided. A bone graft is positioned directly on a conductive mesh frame, which is placed over the bone injury site. A retainer is fastened to the conductive mesh frame and sandwiches the bone graft therebetween. Over the retainer a brace is fastened and further secured to the bony structure directly over the site of the injury. The brace effectively applies pressure on the retainer to effect an intimate contact between the fusion bone and the injury site. An electronic module is further mounted to the brace and coupled to the conductive mesh frame to deliver a stimulating energy to the conductive mesh frame.

34 Claims, 2 Drawing Sheets

APPARATUS FOR DISTRIBUTED BONE GROWTH STIMULATION

TECHNICAL FIELD OF THE INVENTION

This invention relates in general to the field of medical devices. More particularly, the present invention relates to apparatus for distributed bone growth stimulation while providing local stability.

BACKGROUND OF THE INVENTION

The miniaturization of electronic circuits prompted revolutionary advances in many areas of our lives. Some prominent examples range from lap top computers and pocket televisions to global positioning systems and prostheses that provide users with sensory feedback. The advances in electronics have also inspired research and development in the area of orthopedic bone growth stimulation, including the promotion of spinal fusion and healing. This is typically done by implanting electrical current generators in the vicinity of a bone fracture in a patient's body to create a D.C. electric current around the bone fracture. Studies have shown an improved rate of bone growth and fusion when the fractured bone is stimulated in this manner. Other promising stimulation methods include the use of transmitting ultrasound waves through the fracture site.

In addition to bone growth stimulation as outlined above, electronics implanted in the body may also play a role in patient health monitoring. For example, the progress of bone growth may be determined by measuring the amount of electrical resistance of the bone. It is also contemplated that ultrasound imaging is achievable by implanting ultrasound transmitters and receivers at opposed sites and aimed at the locality of interest. A more detailed description of such an ultrasound imaging system may also be found in the above-identified related patent applications.

Conventional methods of implanting electronic circuits, however, give rise to the disadvantage of possible migration of the electrical components, including electronic circuit packages, electrodes and battery packs causing potential shorting of device output. Also, because fracture and fusion sites are mechanically unstable it is common medical practice to provide internal stabilization. Therefore, a need has arisen for apparatus for providing bone growth and fusion stimulation while stabilizing the fractured bone or fusion site. In addition, apparatus for a distributed delivery of the stimulating energy to the injury site is provided.

SUMMARY OF THE INVENTION

In accordance with the present invention, apparatus and a method for bone fixation and stimulation are provided which substantially eliminate or reduce disadvantages and problems associated with prior applications.

In one aspect of the present invention, apparatus for bone fusion by applying a bone graft to a bone injury site is provided. The apparatus comprises a cage mounted directly against the bone injury site for substantially enclosing the bone graft material. A circuit is secured near the bone injury site for generating a stimulating energy and the stimulating energy is delivered to the cage. The bone injury may be traumatically or surgically induced.

In another aspect of the present invention, apparatus for promoting healing in a bony structure having an injury is provided. A plurality of bone grafts are positioned directly on a conductive mesh frame, which is placed over the bone injury site. A retainer is fastened to the conductive mesh frame and sandwiches the bone grafts therebetween. Over the retainer a brace is fastened and further secured to the bony structure directly over the site of the injury. The brace effectively applies pressure on the retainer to effect an intimate contact between the fusion bone and the injury site. An electronic module is further mounted to the brace and coupled to the conductive mesh frame to deliver a stimulating energy to the conductive mesh frame.

An important technical advantage of the present invention provides for a substantially integral device which performs both the function of injury site stabilization and the function of providing stimulation to promote healing. Additionally, through the use of bone graft directly secured to the injury site, bone growth is further encouraged.

BRIEF DESCRIPTION OF THE DRAWINGS

For a better understanding of the present invention, reference may be made to the accompanying drawings, in which.

DETAILED DESCRIPTION OF THE INVENTION

Figure 1:
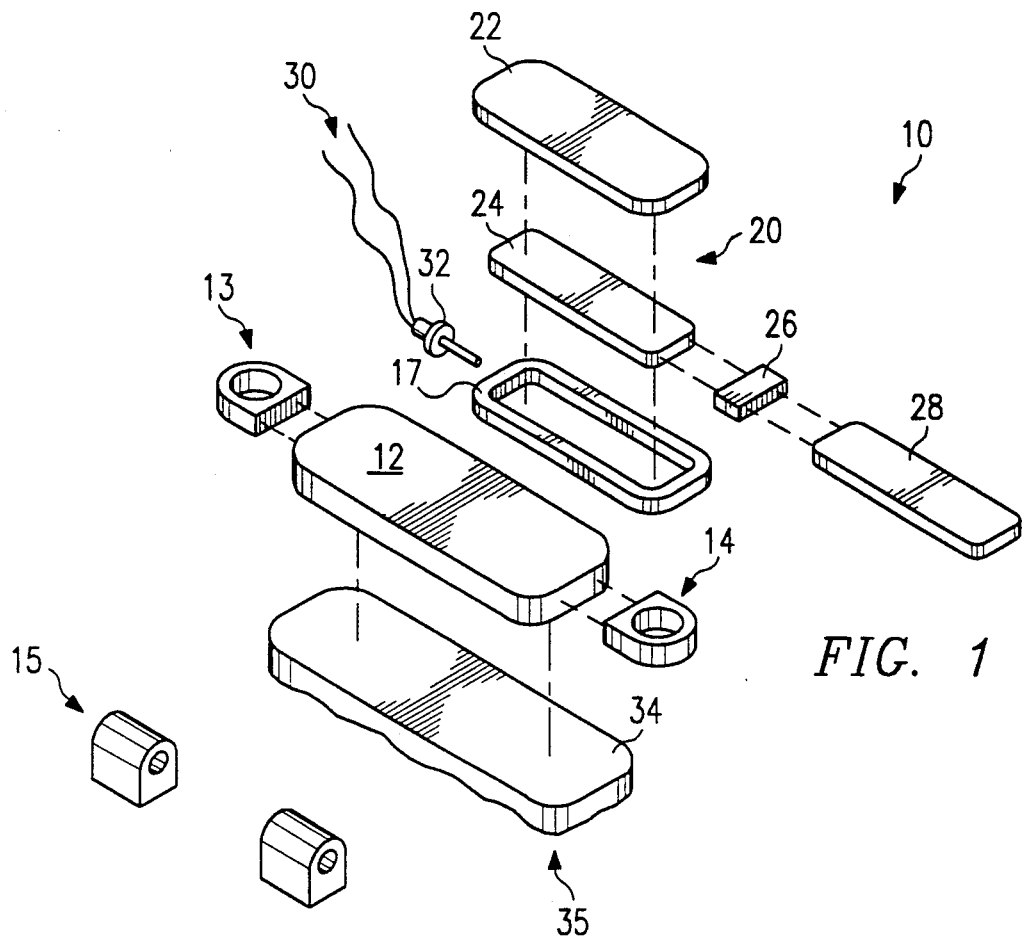
FIG. 1 is an exploded view of one preferred embodiment of the present invention.

With reference to the drawings, FIG. 1 illustrates an exploded view of one embodiment of the apparatus for bone fixation and stimulation, indicated generally at 10 and constructed according to the teaching of the present invention. The embodiment 10 of the present invention comprises parts and optional parts, the designs of which may be stored in a computer aided design (CAD) library (not shown). The parts are selectable from the CAD library by a physician or practitioner in accordance with the predefined needs of the patient. For example, if it is determined that an electric field stimulation in combination with a resistance reading and telemetry is desired for optimal healing promotion and monitoring for a particular patient, then apparatus 10 may be constructed with those parts selected from the library which perform these functions.

Apparatus 10 comprises a base plate 12, which includes fixation means 13 and 14 which provide firm coupling between base plate 12 and the underlying bone (not shown). Fixation means 13 and 14 may include openings, lying in the same plane as base plate 12 or in any plane of orientation, for receiving fasteners which secure base plate 12 to the underlying bone. The openings in fixation means 13 and 14 may be formed integral to base plate 12 or be constructed independently and then attached to base plate 12, as shown. Alternatively, apparatus 10 may be constructed by a stereolithographic method, so that all selected parts are fashioned integrally from a single piece of raw material, such as implantable grade titanium, stainless steels, cobalt chrome steels or appropriate plastics, ceramics and carbon fibre composites.

Figure 3:
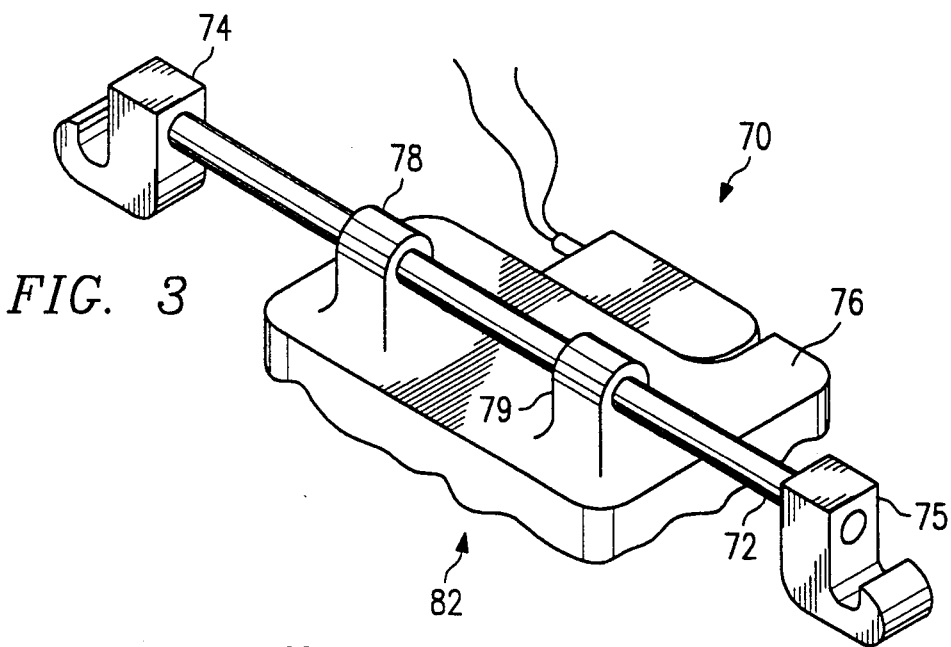
FIG. 3 is a perspective view of yet another preferred embodiment of the present invention.

Alternatively, fixation means 13 and 14 may include means 15 for accepting a rod (an example of which is shown in FIG. 3) for fastening apparatus 10 to the underlying bone structure. This manner of stabilization is especially suited to providing fixation for injured spinal columns.

Onto base plate 12 an electronic module housing 17 may be formed which encloses an electronic module 20, along with a cover plate 22. Ideally, the inner cavity of housing 17 follows the outer contours of electronic module 20 closely and without substantial unused space. It is also preferable that electronic module 20 includes an insulative housing 24 which houses the electronic circuitry (not shown). In cases in which more than one electronic module is required, an interconnect device 26 may be used to couple electronic module 20 with an additional module 28, for example. Housing 17 and cover plate 22 may be expanded accordingly to accommodate the additional electronic module 28 and interconnect device 26. Additional parts, electrodes 30 for delivering the electric energy to the bone structure, for example, are provided. Electrodes 30 are connectable to electronic module 20 by a connector 32 that may have a threaded coupling with housing 17.

Apparatus 10 is shown in an exploded view in FIG. 1 to better display each independent part. However, once the parts deemed desirable for a specific application are selected, the resultant apparatus 10 is preferably of an integral construction. For example, all parts including fastening means 13, 14 or 15, base plate 12, and housing 17 (except electronic modules 20 and 28, module interconnector 26 and cover plate 22) may be constructed by forming and/or molding a single piece of material. Additionally, an interface plate 34 which may be formed integral with base plate 12 is provided. A surface 35 of interface plate 34 may have been prepared by rastographic data gathering, computer aided design, and stereolithographic modeling, so that the surface contour thereof is an inverse image of the bone surface to which apparatus 10 is to be affixed. In this manner, an intimate mating surface is provided to ensure substantially non-slippage and non-migration of apparatus 10 with respect to the underlying bone structure. Apparatus 10 further comprises a cage means, defined in part by housing 17, and cover plate 22, for holding a bone graft to the injury site and a fixation means of stabilizing the bone injury.

Figure 2:
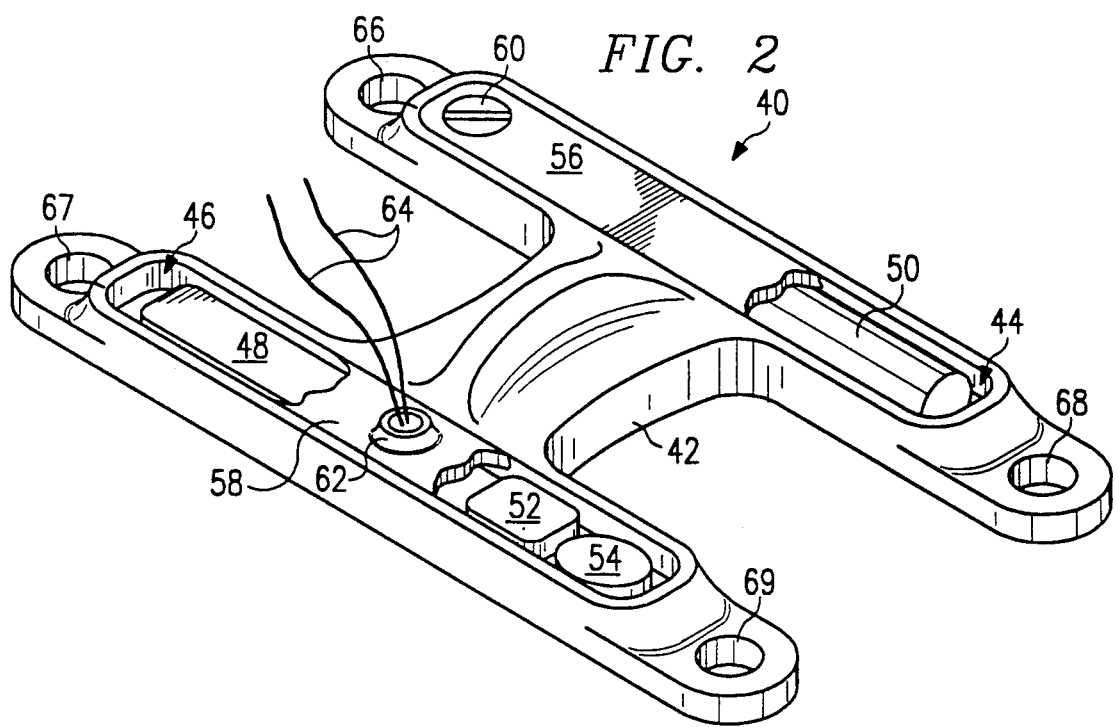
FIG. 2 is a perspective view of another preferred embodiment of the present invention, portions of which are cut away to provide a view of the electronic modules.

Referring to FIG. 2 for an alternate embodiment of the present invention, a perspective view of a generally H-shaped apparatus 40 for bone fixation and stimulation is shown. Apparatus 40 comprises a generally H-shaped brace structure 42 having cavities 44 and 46 for housing electronic modules 48-52 that perform, for example, bone stimulation, healing monitoring, telemetry, pain control and other functions. As discussed above, apparatus 40 can be tailored to encompass electronic module functions deemed necessary for a particular patient. In addition, a battery 54 may be included to provide the necessary electrical power to electronic modules 48-52. Cavities 44 and 46 are enclosed by cover plates 56 and 58, which may be secured by fasteners 60 or may be welded to form a substantially air-tight seal. Additionally, cover plates 56 and 58 may have openings 62 to 65 allow electrode wires 64 to pass through, for example. Apparatus 40 may be fastened to the injured bone site by applying fasteners (not shown), such as bolts or screws and the like through openings 66-69. Apparatus 40 further comprises a cage means, defined in part by brace structure 42, cavities 44 and 46, and cover plates 56 and 58, for holding a bone graft to the injury site and a fixation means of stabilizing the bone injury.

Referring to FIG. 3, yet another embodiment of the present invention is shown. Apparatus 70 employs a rod fixation method, which uses a rod 72 with hook-like structures 74 and 75 at each respective end. Hook-like structures 74 and 75 are designed to be hooked onto certain features of the vertebrae in the spinal column in order to firmly secure apparatus 70 at or near the site of injury and to stabilize an injured vertebra or disc. Rod 72 is attached to a base plate 76 by inserting it through saddle-like structures 78 and 79, which are either firmly attached to base plate 76 or formed integrally therewith as one unit. Preferably, base plate 76 has a surface 82 that substantially conforms to the features of the injured bone to which apparatus 70 is to be affixed. As mentioned above, surface 82 may be constructed by way of rastographic data gathering, computer aided design and stereolithographic modeling.

Figure 4:
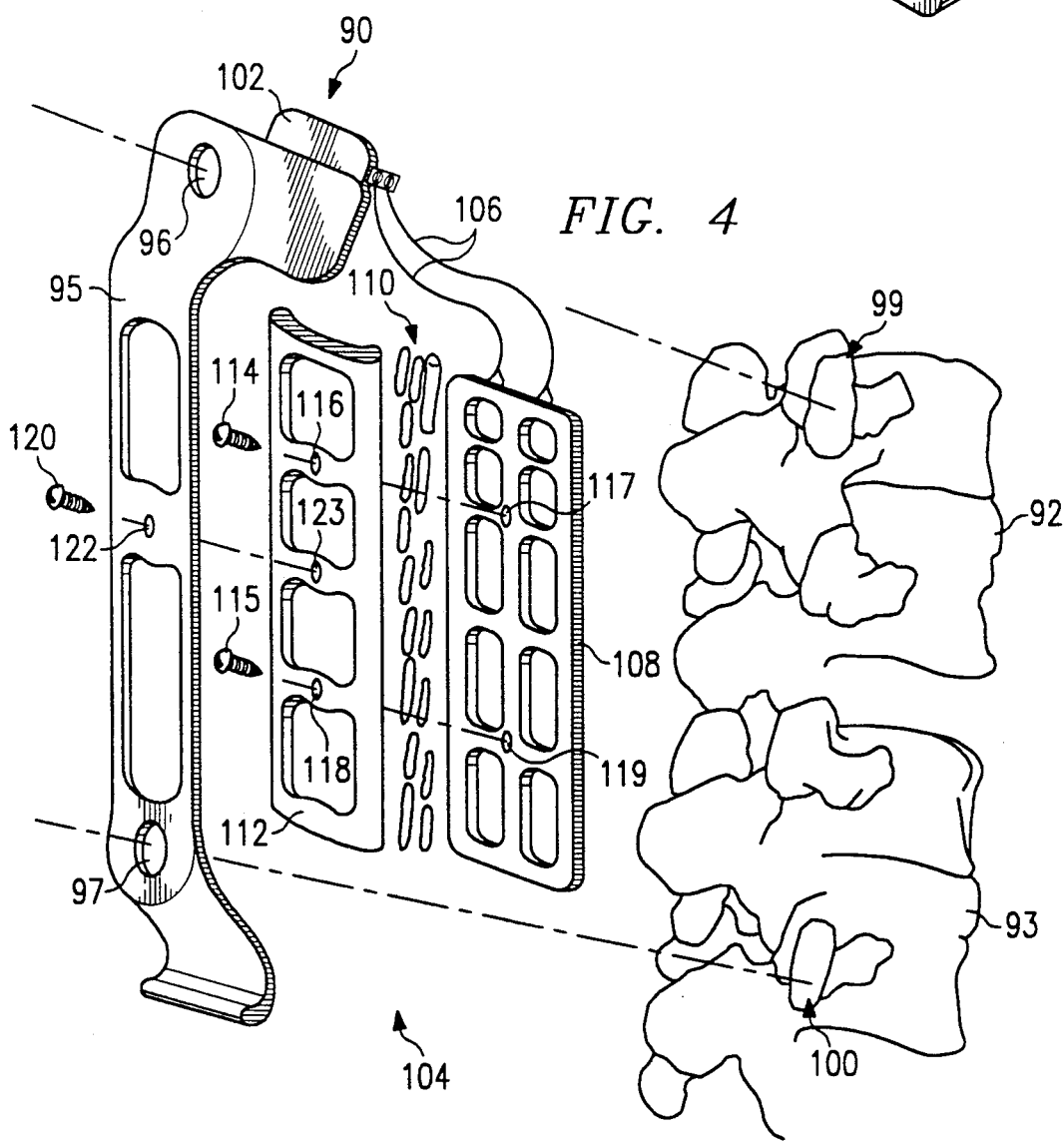
FIG. 4 is an exploded view of yet another embodiment of the present invention.

Referring to FIG. 4, where an exploded view of yet another embodiment of the present invention is shown. Apparatus 90, as shown, is constructed to provide fixation and primarily stimulation to an injury site located between two vertebrae 92 and 93 on a spinal column. The injury may be, for example, a segmental instability which requires vertebrae 92 and 93 on either side of the injured disc to remain fixed with respect to one another while fusion healing takes place.

Apparatus 90 comprises a fixation brace 95 shaped and contoured to follow closely the site of attachment on the spine. The contouring may be achieved by the rastographic data gathering, computer aided design and stereolithographic method described above, with the objective of realizing a brace which is custom made to fit unique fixation sites of individual patients. Brace 95, as shown in FIG. 4, is elongated and has two ends. At both ends, holes 96 and 97 are provided to receive screws (not shown) which fasten apparatus 90 to sites 99 and 100 on vertebrae 92 and 93, respectively. Note that other fastening means, such as the rod arrangement shown in FIG. 3, are also applicable in this embodiment.

Attached to brace 95 is an electronic module 102. Electronic module 102 may perform a myriad of functions including bone fusion stimulation, telemetry, fusion monitoring, and the like as described above. However, in the present embodiment, a field distribution device 104 is provided to improve the operation of electric field stimulation. Electronic module 102 may be contained within a cavity within brace 95 or merely coupled thereto as shown. A pair of electrode wires 106 extend from electronic module 102 and are coupled to a mesh electrode frame 108. Mesh electrode frame 108 is constructed of a substantially conductive and generally flexible material. It comprises a mesh frame that offer improved distribution of electromagnetic energy at and surrounding the injury site, and thus promotes an increased rate of healing.

On top of mesh electrode frame 108 is overlaid bone fragments or bone graft 110, and a bone graft retainer 112. Fusion bones 110 are thus sandwiched between mesh electrode frame 108 and retainer 112 and held together by fasteners 114 and 115. Fasteners 114 and 115 are preferably screws which are inserted through threaded apertures 116-117 and 118-119, in retainer 112 and mesh electrode frame 108, respectively. Field distribution device 104 is further coupled to brace 95 by a fastener, such as screw 120 which is adapted to be received by threaded apertures 122 and 123 in brace 95 and retainer 112, respectively. Apparatus 40 further comprises a cage means, defined in part by mesh electrode frame 108, retainer 112 and brace 95.

In operation, electronic module 102 delivers an electric current to mesh electrode frame 108 via wire electrodes 106. Stimulated by the electric current in mesh electrode frame 108, fusion bones 110 grow together and fuse to the area between vertebrae 92 and 93 at an enhanced rate. When fusion is complete, brace 95 and fusion bone retainer 112 along with electronic module 102 may be removed from the site.

Although the present invention has been described in detail, it should be understood that various changes, substitutions and alterations can be made thereto without departing from the spirit and scope of the present invention as defined by the appended claims.

What is claimed is:

1. Apparatus for bone fusion comprising a cage means for substantially enclosing a bone graft at a bone injury site and said cage means adapted to be mounted directly against the bone injury site.

2. The apparatus, as set forth in claim 1, further comprising:
   circuit means adapted to be secured near the bone injury site for generating a stimulating energy; and
   conductive means for coupling said circuit means and said cage means, said cage means receiving and being energized by said stimulating energy.

3. The apparatus, as set forth in claim 1, wherein said cage means comprises:
   a conductive mesh frame; and
   a retainer fastened to said conductive mesh frame and sandwiching a plurality of bone grafts therebetween.

4. The apparatus, as set forth in claim 1, further comprising a brace detachably coupled to said cage means and further adapted to be detachably secured over the bone injury site, said brace applying pressure against said cage means toward the bone injury site to effect an intimate contact therebetween.

5. The apparatus, as set forth in claim 4, wherein a circuit means, adapted to be secured near the bone injury site for generating and monitoring a stimulating energy, is coupled to and housed in said brace.

6. The apparatus, as set forth in claim 5, wherein said brace defines a cavity adapted for housing said circuit means.

7. The apparatus, as set forth in claim 4, wherein said brace further comprises a contoured surface adapted to be closely matched to the contour of a bony structure at and surrounding the bone injury site.

8. The apparatus, as set forth in claim 4, wherein said brace further comprises at least one portion coming into contact with at least one point on a bony structure surrounding the bone injury site, the contour of said portion being adapted to be closely matched to the contact point on said bony structure.

9. The apparatus, as set forth in claim 1, wherein said cage means is substantially flexible.

10. Apparatus for promoting healing in a bony structure having an injury, comprising:
    a conductive mesh frame;
    a bone graft positioned directly on said conductive mesh frame;
    a retainer fastened to said conductive mesh frame and sandwiching said bone graft therebetween;
    a brace fastened to said retainer and further adapted to be secured to said bony structure directly over the site of the injury, said brace effectively pressing said conductive mesh frame, said bone graft and said retainer against the injury site and stabilizing said bony structure; and
    an electronic module being mounted to said brace and coupled to said conductive mesh frame, said electronic module housing an electronic circuit for delivering a stimulating energy to said conductive mesh frame.

11. The apparatus, as set forth in claim 10, wherein said injury is between a plurality of vertebrae, said brace adapted to be fastened to said vertebrae and holding said conductive mesh bone graft directly over the site of the injury.

12. The apparatus, as set forth in claim 10, wherein said conductive mesh frame is substantially flexible.

13. The apparatus, as set forth in claim 10, wherein said brace further comprises a contoured surface adapted to be closely matched to the contour of said bony structure.

14. The apparatus, as set forth in claim 13, wherein said brace further comprises at least one portion coming into contact with at least one point on said bony structure, the contour of said portion being adapted to be closely matched to the contour of the said bony structure at the contact point.

15. The apparatus, as set forth in claim 10, wherein said retainer is fastened to said conductive mesh frame with fasteners.

16. The apparatus, as set forth in claim 10, wherein said brace is fastened to said retainer with fasteners.

17. The apparatus, as set forth in claim 10, wherein said brace is adapted to be secured to said bony structure with screws.

18. The apparatus, as set forth in claim 10, wherein said brace further comprises a rod having a hook-like member on each end of the rod, said hook-like members being adapted for hooking onto designated features of said bony structure and securing said brace thereto.

19. Apparatus for promoting healing in a bony structure having an injury, comprising:
    a bone graft;
    a conductive mesh housing for containing said bone graft;
    a brace overlying said conductive mesh housing and fastened thereto, and further adapted to be secured to said bony structure directly over the site of the injury, said brace effectively pressing said conductive mesh housing and said bone graft against the injury site and immobilizing said bony structure; and
    an electronic module being mounted to said brace and coupled to said conductive mesh housing, said electronic module delivering a stimulating energy to said conductive mesh housing.

20. The apparatus, as set forth in claim 19, wherein said injury is a segmental instability between a plurality of spinal vertebrae, said brace adapted to be fastened to said vertebrae and holding said conductive mesh housing and bone graft directly over the site of said segmental instability.

21. The apparatus, as set forth in claim 19, wherein said conductive mesh housing is substantially flexible.

22. The apparatus, as set forth in claim 19, wherein said brace further comprises a contoured surface adapted to be closely matched to the contour of said bony structure.

23. The apparatus, as set forth in claim 22, wherein said brace further comprises at least one portion coming into contact with at least one point on said bony structure, the contour of said portion being adapted to be closely matched to the contour of the said bony structure at the contact point.

24. The apparatus, as set forth in claim 19, wherein said brace is fastened to said conductive mesh housing with fasteners.

25. The apparatus, as set forth in claim 19, wherein said brace is adapted to be secured to said bony structure with screws.

26. The apparatus, as set forth in claim 19, wherein said brace further comprises a rod having a hook-like member on each end of the rod, said hook-like members being adapted for hooking onto designated features of said bony structure and securing said brace thereto.

27. Apparatus for promoting healing in a bony structure having injury, comprising:
a bone graft;
conductive means having a plurality of small openings for retaining said bone graft;
a brace adapted to fasten said conductive means and said bone graft to said bony structure directly over the site of injury, said brace adapted to effectively immobilize said bony structure; and
an electronic circuit mounted to said brace for delivering a stimulating energy to said conductive means.

28. The apparatus, as set forth in claim 27, wherein said injury is between a plurality of vertebrae, said brace adapted to be fastened to said vertebrae and holding said conductive means and a plurality of bone grafts directly over the injury site.

29. The apparatus, as set forth in claim 27, wherein said conductive means is substantially flexible.

30. The apparatus, as set forth in claim 27, wherein said brace further comprises a contoured surface adapted to be closely matched to the contour of said bony structure.

31. The apparatus, as set forth in claim 30, wherein said brace further comprises at least one portion coming into contact with at least one point on said bony structure, the contour of said portion being adapted to be closely matched to the contour of the said bony structure at the contact point.

32. The apparatus, as set forth in claim 27, wherein said brace is fastened to said conductive means with fasteners.

33. The apparatus, as set forth in claim 27, wherein said brace is adapted to be secured to said bony structure with screws.

34. The apparatus, as set forth in claim 27, wherein said brace further comprises a rod having a hook-like member on each end of the rod, said hook-like members being adapted for hooking onto designated features of said bony structure and securing said brace thereto.

* * * * *

UNITED STATES PATENT AND TRADEMARK OFFICE
CERTIFICATE OF CORRECTION

PATENT NO. : 5,304,210
DATED : April 19, 1994
INVENTOR(S) : Crook

It is certified that error appears in the above-identified patent and that said Letters Patent is hereby corrected as shown below:

Column 6, line 17, after "mesh", insert -- and --.

Column 7, line 23, after "having", insert -- an --.

Signed and Sealed this

Twenty-fifth Day of April, 1995

Attest:

BRUCE LEHMAN

Attesting Officer          Commissioner of Patents and Trademarks